(12) United States Patent
Erickson et al.

(10) Patent No.: US 8,552,363 B2
(45) Date of Patent: Oct. 8, 2013

(54) SYSTEM AND METHOD FOR OPTICALLY DRIVEN SEPARATIONS USING FLUID FILLED CORE OPTICAL FIBERS

(75) Inventors: David Erickson, Ithaca, NY (US); Sudeep Mandal, Ithaca, NY (US)

(73) Assignee: Cornell University, Ithaca, NY (US)

( * ) Notice: Subject to any disclaimer, the term of this patent is extended or adjusted under 35 U.S.C. 154(b) by 325 days.

(21) Appl. No.: 12/143,952

(22) Filed: Jun. 23, 2008

(65) Prior Publication Data

US 2009/0032730 A1 Feb. 5, 2009

Related U.S. Application Data

(60) Provisional application No. 60/929,301, filed on Jun. 21, 2007.

(51) Int. Cl.
*H01S 3/00* (2006.01)
(52) U.S. Cl.
USPC .......................... 250/251; 250/435; 385/129
(58) Field of Classification Search
USPC .......................................................... 250/251
See application file for complete search history.

(56) References Cited

U.S. PATENT DOCUMENTS 6,784,420 B2 * 8/2004 Wang et al. .................. 250/251
7,366,377 B2 * 4/2008 Getin et al. .................... 385/37
7,444,053 B2 * 10/2008 Schmidt et al. ............... 385/129

OTHER PUBLICATIONS

Grier DG, A revolution in optical manipulation, (2003), Nature 424 (6950): 810-816.
Neale SL, MacDonald MP, Dholakia K, Krauss TF; All-optical control of microfluidic components using form birefringence, (2005), Nature Materials 4 (7): 530-533.
Chiou PY, Ohta AT, Wu MC; Massively parallel manipulation of single cells and microparticles using optical images, (2005), Nature 436 (7049): 370-372.
Wang MM, Tu E, Raymond DE, Yang JM, Zhang HC, Hagen N, Dees B, Mercer EM, Forster AH, Kariv I, Marchland PJ, Butler WF; Microfluidic sorting of mammalian cells by optical force switching, (2005), Nature Biotechnology 23 (1): 83-87.
Curtis JE, Koss BA, Grier DG; Dynamic holographic optical tweezers, (2002), Optics Communications 207 (1-6): 169-175.
Svoboda K, Block SM; Optical Trapping of Metallic Rayleigh Particles (1994), Optics Letters 19 (13): 930-932.
Neuman KC, Block SM; Optical Trapping (2004), Review of Scientific Instruments 75 (9): 2787-2809.
Ashkin A, Gordon JP; Stability of Radiation-Pressure Particle Traps-an Optical Earnshaw Theorem (1983), Optics Letters 8 (10): 511-513.
MacDonald MP, Spalding GC, Dholakia K; Microfluidic sorting in an optical lattice (2003), Nature 426 (6965): 421-424.

(Continued)

*Primary Examiner* — Phillip A Johnston
(74) *Attorney, Agent, or Firm* — Perkins Coie LLP

(57) ABSTRACT

An optical chromatography system employs fluid filled hollow core fibers, such as photonic crystal fibers (PCFs), which confine an incident optical beam from a laser, for example, in the core and cause separation of particles in the fluid along the length of the PCF. The incident optical beam is confined in the fluid filled core of the PCF by a periodic lattice of air capillaries surrounding the core. The lattice either creates a lower refractive index in the cladding than in the fluid filled core or creates a 1D photonic bandgap structure where the guiding is accomplished by surrounding the fluid filled core with a periodically changing array of dielectric constant which prohibits radial dilution of the optical energy over a range of wavelengths through photonic bandgap effects.

36 Claims, 3 Drawing Sheets

(56) References Cited

OTHER PUBLICATIONS

Hatano T, Kaneta T, Imasaka T; Application of optical chromatography to immunoassay (1997), Analytical Chemistry 69 (14): 2711-2715.

Imasaka T, Optical chromatography. A new tool for separation of particles (1998), Analysis 26 (5): M53-M55.

Makihara J, Kaneta T, Imasaka T; Optical Chromatography: Size determination by eluting particles (1999), Talanta 48 (3): 551-557.

Kaneta T, Ishidzu Y, Mishima N, Imasaka T; Theory of optical chromatography (1997), Analytical Chemistry 69 (14): 2701-2710.

Zhao BS, Koo YM, Chung DS; Separations based on the mechanical forces of light (2006), Analytica Chimica Acta 556 (1): 97-103.

Hart SJ, Terray AV; Refractive-index-driven separation of colloidal polymer particles using optical chromatography (2003), Applied Physics Letters 83 (25): 5316-5318.

Hart SJ, Terray A, Kuhn KL, Arnold J, Leski TA; Optical chromatography of biological particles (2004), American Laboratory 36 (24): 13-.

Terray A, Arnold J, Hart SJ; Enhanced optical chromatography in a PDMS microfluidic system (2005), Optics Express 13 (25): 10406-10415.

Hart SJ, Terray A, Leski TA, Arnold J, Stroud R; Discovery of a significant optical chromatographic difference between spores of *Bacillus anthracis* and its close relative, *Bacillus thuringiensis* (2006), Analytical Chemistry 78 (9): 3221-3225.

\* cited by exam

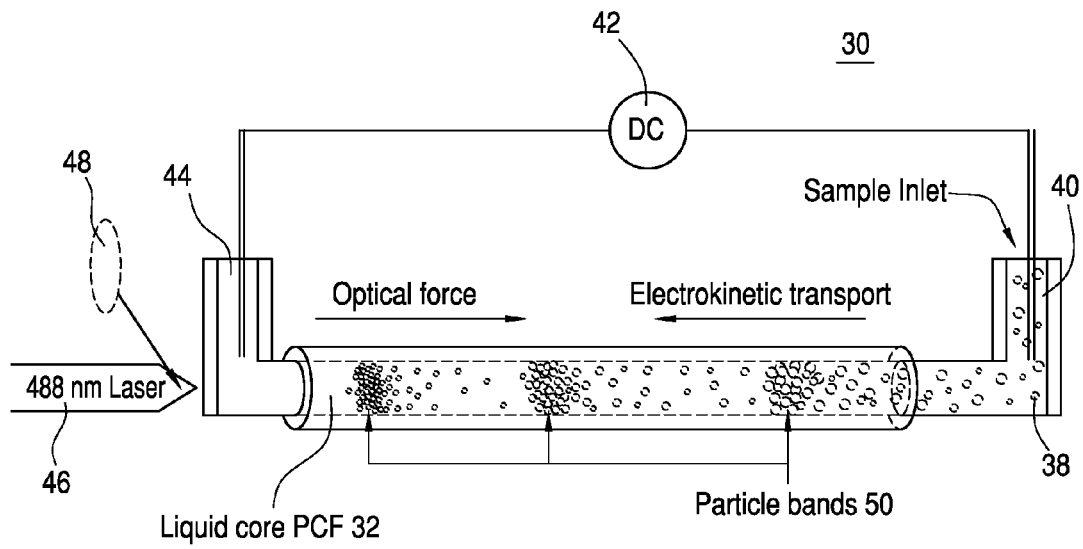
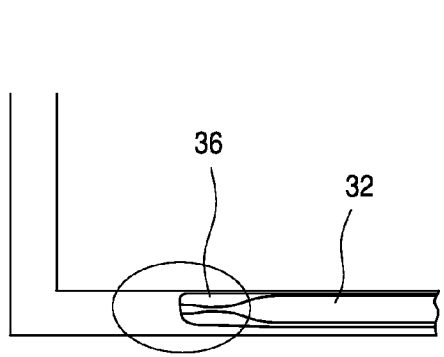 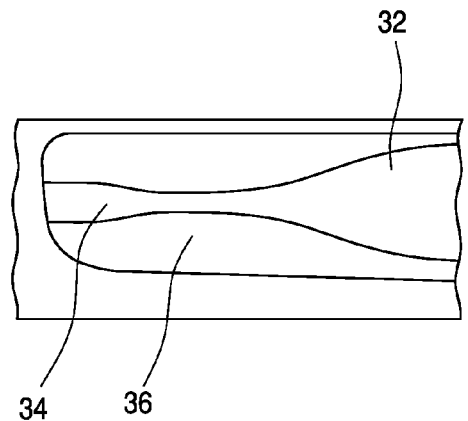
FIG. 2A
FIG. 2B  FIG. 2C

SYSTEM AND METHOD FOR OPTICALLY DRIVEN SEPARATIONS USING FLUID FILLED CORE OPTICAL FIBERS

CROSS REFERENCE TO RELATED APPLICATIONS

This application claims the benefit, under 35 U.S.C. 119(e), of U.S. Provisional Application No. 60/929,301, filed Jun. 21, 2007, which is hereby incorporated by reference in its entirety.

BACKGROUND OF THE INVENTION

1. Field of the Invention

The present invention relates, in general, to optical chromatography systems and methods that employ optical fibers, such as photonic crystal fibers, that are configured to confine light in a fluid filled core and thereby facilitate separation of particles or other targets in the fluid based on size or other properties.

2. Description of the Background Art

Free-space optical manipulation techniques in microfluidic systems have recently generated a significant amount of interest. Such techniques range from traditional optical tweezing (see a recent review by Grier [1]), rotational manipulation of components based on form birefringence [2] to a more recent electro-optic approach such as that by Chiou et al. [3]. As an example of a direct device integration, Wang et al. [4] developed an optical force based cell sorting technique whereby radiation pressure was used to direct rare cells into a separate streams following a green florescent protein (GFP) detection event. Classically the advantage of these optical approaches lies in their ability to provide remote operation and handle individual particles directly as opposed to indirect manipulation of the surrounding flow field.

Though very subtle and complex manipulations have been demonstrated (e.g. Curtis et al. [5]), the majority of these implementations tend to be "binary". This means that they rely on either the ability to trap or not trap a particle based on whether the conditions for trapping stability are met [6-8]. Recently however a number of works have extended these ideas to exploit the dependence of this trapping potential on the particle properties, enabling much more advanced and subtle operations. As an example, Macdonald et al. [9] demonstrated an optical lattice technique where particles of different sizes were sorted into different streams depending on their strength of repulsion to regions of high optical intensity. In a series of papers, Imasaka and coworkers [10-13] provided the initial foundations for optically driven separation techniques, which they termed optical chromatography (see a recent review by Zhao et al. [14]). These works have recently been extended by Hart et al. who have demonstrated refractive index separation of colloids [15] and other bioparticles [16]. They have also recently integrated this into a microfluidic device format for pathogen detection [17], demonstrating very precise separation between very closely related bacteria *Bacillus anthracis* and *Bacillus thuringiensis* and millimeter scale separation [18]. The potential advantage of "Optical Chromatography" is that the propulsive velocity has as much as a $5^{th}$ power dependence on particle radius. Thus while this technique would not be suitable for cases where de-mixing is undesirable, it would enable as much as 3 orders of magnitude more resolute separations than the current state of the art.

The precision with which particles can be transported and separated with these optical techniques makes them particularly useful for biomedical analysis devices. At present, however, these systems are practically limited by the fundamentals of the free-space optics on which they rely. Specifically, the systems rely on an incident optical beam which is focused by an objective lens on the particles to be separated. The resulting light beam-particle interaction length is limited by either the focal depth or the spot size of the objective lens to usually a few hundred microns. Using a more loosely focused lens (larger spot size) increases the interaction length perhaps to around a millimeter. The required power however scales with the square of the beam radius and as such relatively large optical power is required to perform manipulations over even these relatively small length scales (e.g. Hart et al. [15, 16, 18] used a 700 mW laser to achieve mm scale separation).

SUMMARY OF THE INVENTION

The present invention solves the foregoing problem through provision of an optical fiber based optical chromatography system and method. Preferably, the optical fiber is a photonic crystal fiber (PCF) with a fluid filled hollow core; however, other optical fibers that can guide light in a fluid core could also be employed. Hollow core PCFs consist of a periodic lattice of air capillaries surrounding the core which creates a photonic bandgap in the cladding causing light of the corresponding wavelengths (i.e. those which are within the bandgap) to be guided within the hollow core. In the current preferred embodiments, the hollow core is selectively filled with aqueous based solutions. Because this changes the refractive index of the core, the PCF now guides light via a total internal reflection mechanism because the refractive index of the liquid filled core is higher than the average cladding index. In general, however, confining light in the core via a bandgap mechanism or refractive index confinement mechanism are both equally valid techniques that can be employed in the present invention.

In its broadest sense, the present invention thus involves a particle separation technique in which any fluid (i.e. liquid or gas) core fiber waveguiding structure is employed wherein an incident optical beam is confined in the fluid core and causes particles in the fluid to be separated along the length of the core based on size or other optical radiation responsive properties. In one embodiment, this is accomplished by refractive index difference in which a liquid core is employed that has a greater refractive index than the effective refractive index of the medium surrounding the liquid core. An example of how this has been done is by using a PCF with air filled passages in its cladding. In another embodiment, a PCF is used having a 1D photonic bandgap structure where the guiding is accomplished by surrounding the fluid core with a periodically changing array of dielectric constant which prohibits radial dilution of the optical energy over a range of wavelengths through a photonic bandgap effect. A light source, such as a laser, generates an optical beam that is focused and optically coupled into the optical fiber. Target particles to be separated are inserted into the liquid core of the waveguide using any suitable technique, such as a microfluidic technique. The optical beam causes the particles to move different distances along the waveguide, depending on their size or other optically responsive property. The resulting position of the particles after separation can be optically or electrically detected using any suitable technique as well. Example implementations of the invention have demonstrated that the particles can be moved upwards of 1 meter or more along the length of the fiber, which represents a dramatic improvement over the millimeter magnitude lengths of prior optical separation systems.

The use of a liquid core fiber (LCF) thus solves the main difficulty with existing optical chromatography devices since the LCF system confines light by one of the two mechanisms described above over very long distances with very little lengthwise dilution of the optical energy (e.g. in telecommunications for example optical fibers carry signals over kilometer scale distances) while providing full access to the optical mode. The present invention thus represents the first known practical technology that can take advantage of the exceptional potential of optically driven separations.

BRIEF DESCRIPTION OF THE DRAWINGS

The foregoing and other features and advantages of the invention are described in detail below, in conjunction with the accompanying drawings, which are briefly described as follows.

FIG. 1A shows the cross section of a hollow core PCF. FIG. 1B is a schematic diagram showing introduction of particles in a liquid sample into the hollow core of a PCF.

FIG. 2A is a schematic illustration of a first implementation of an optofluidic chromatography system constructed in accordance with a first preferred embodiment of the present invention which comprises an integrated system that incorporates a flow through counter direction electroosmotic flow. FIG. 2B is a close up view of the circled section in FIG. 2A, while FIG. 2C is a close up view of the circled section in FIG. 2B. These show how PDMS microfluidics structures can be used in the preferred embodiments to introduce a fluid sample into the hollow core of a PCF.

In FIG. 3A, the initial sample is introduced into fiber in the same manner as with capillary electrophoresis. In FIG. 3B, after optical excitation, separated particles or targets are detected and removed at the capillary exit.

DETAILED DESCRIPTION OF THE PREFERRED EMBODIMENTS

Figure 1A:
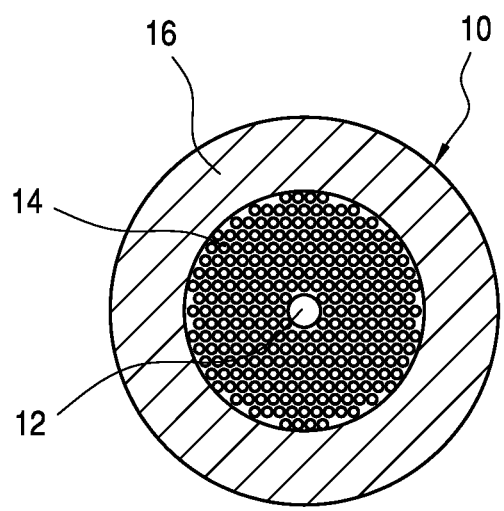
FIGS. 1A and 1B are schematic diagrams showing how optofluidic transport occurs in a Liquid Core Photonic Crystal Fiber (LCPCF) in accordance with the concepts of the present invention.
Figure 1B:
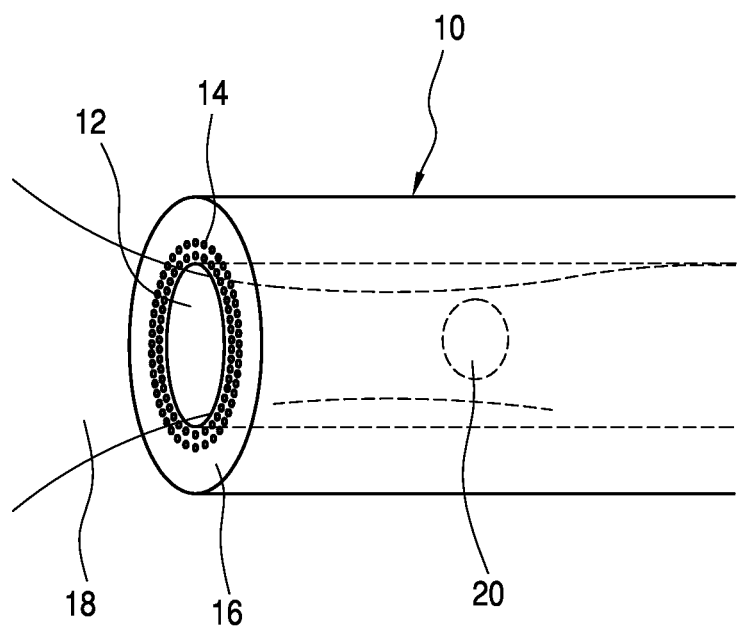

With reference first to FIGS. 1A and 1B, the basic concept employed in all embodiments of the present invention were first tested experimentally and confirmed. In the experiments, a 20 µm diameter core hollow-core PCF Crystal Fiber 10 (HC19-1550-01) was used. A cross section of the PCF 10 is shown in FIG. 1A. The PCF 10 includes a hollow core 12 which was filled with an aqueous solution during the experiments, a plurality of air-filled capillaries 14 surrounding the hollow core 12 and a solid outer cladding 16. The use of the air filled capillaries 14 effectively lowers the overall index of refraction of the capillaries and the cladding 16 below that of the liquid filled core 12 so that any light that is coupled into the core 12 will be confined in and travel along the length of the core 12.

In the experiments, to fill only the hollow core 12 with liquid, the ends of the capillaries 14 at the fiber mouth were closed, while leaving the core 12 open. To achieve this, UV curing and fusion splicing techniques were considered and evaluated. Both techniques worked, though the fusion splicing technique was used in the experiments because it was found to be more reliable. High temperatures during the fusion process cause the small capillaries 14 to collapse into each other, while the central core 12 remains largely unaffected due to its larger diameter.

A 488 nm argon-ion laser was employed to generate the optical beam, which was made incident on a 4× microscope objective to couple it into the fiber core 12. The PCF 10 was then dipped in a glass container filled with a dilute aqueous solution of 3 µm fluorescent polystyrene beads. FIG. 1B illustrates the PCF 10 with an aqueous solution 18 in the core 12 and one of the beads 20 in the solution 18.

A 40× objective at the other end of the fiber was used to image the near field pattern of the emerging laser beam. This was required to ensure that the light is being coupled into the core because slight misalignments can lead to light coupling into the silica cladding. A charge coupled device camera with an attached microscope objective was used to image particles rising up the immersed tip of the fiber. Initially the fiber end was dipped in de-ionized water and the fiber was aligned so as to couple light into it.

Once proper light guidance through the liquid filled core was confirmed, small quantities of 3 µm fluorescing polystyrene particles were introduced into the water. As expected, particles in the path of the 488 nm laser beam were pushed axially upwards through the fiber end. The ultimate travel distance of the particles was strongly dependent on the quality of the optical coupling. In some cases, particles were transported over distances of greater than 2 cm with a laser excitation power of 210 mW measured at the laser output.

A notable observation during the experiments was the concentration of similar 3 µm polystyrene particles into distinct "floating bands" within the liquid core of the PCF. The concentrated band showed almost no transport based sample dispersion. This banding was demonstrated at excitation powers as low as 50 mW and it was observed that these bands can comprise an extremely large number of particles; no upper limit was detected here. The axial resting place of the floating band was shown to rise with increasing incident power and vice versa. As mentioned earlier, at a particular height the axial scattering force is exactly balanced by the weight of the particle and loss induced gradient force. Mode hopping was also observed to vary the absolute location of the band along the transport axis but did not result in any observable dispersion. This antidispersive concentrating effect is believed to result from a sharp localized drop in the field intensity as a result of scattering at the band location. The resulting change in field intensity strongly enhances the local gradient force pulling particles into the formations while maintaining a strong scattering force acting from below.

As a result of the foregoing experiments, which confirmed the operational principle of the present invention, a number of implementations of the invention were developed. In its broadest sense, the present invention involves a particle separation technique in which any fluid core waveguiding fiber structure is employed wherein an incident optical beam is confined in the fluid core and this confinement causes particles in the fluid to be separated along the length of the core. In one embodiment, this is accomplished as in the experiment by refractive index difference where the core is filled with liquid having a refractive index that is greater than the effective refractive index of the medium surrounding the liquid core by using a PCF with air filled passages in its cladding. In another embodiment, a PCF is used having a 1D photonic bandgap structure where the guiding is accomplished by surrounding the fluid filled core with a periodically changing array of dielectric constant which prohibits radial dilution of the optical energy over a range of wavelengths through photonic bandgap effects.

A light source generates an optical beam that is focused and optically coupled into the optical fiber. The light source can be either coherent or incoherent, though a laser light source is preferred. Target particles to be separated are inserted into the fluid filled core of the waveguide using any suitable technique, such as a microfluidic technique. The optical beam causes the particles to move different distances along the fiber core, depending on their size or other optically responsive properties. The resulting position of the particles after separation can be optically or electrically detected using any suitable technique as well. Example implementations of the invention have demonstrated that the particles can be moved upwards of 1 meter or more along the length of the fiber waveguide, which represents a dramatic improvement over the millimeter magnitude lengths of prior optical separation systems.

Example implementations will now be provided to demonstrate how each of the foregoing components can be enabled into a specific device technology. The first implementation comprises an optical chromatography system 30 that employs a horizontal configuration with a counter electroosmotic flow as shown in FIGS. 2A-2C. This causes a drag force on the particles analogous to gravity. Using this technique the particles will separate into bands each containing a different population of species based on their size or dielectric constant.

In the system 30, the liquid core waveguiding structure, in this case a liquid core photonic crystal fiber 32, is embedded in a channel 34 of a PDMS microfluidic system 36 as shown in the close up illustrations of FIGS. 2B and 2C. It should be noted that the microfluidics do not have to be fabricated from PDMS, however, this facilitates the integration. Particles 38 are then introduced into the PCF 32 via electrokinetic flow, which is done simply by putting the particles in an upstream reservoir 40 and applying a source of voltage 42 between the upstream reservoir 40 and a downstream reservoir 44. Light is coupled into the PCF 32 by optically exciting the downstream end of the fiber through the PDMS microfluidics 36. This requires that the edge of the PDMS chip be relatively flat and that the channel go through a quick turn near the downstream end of the fiber 32 as shown in FIG. 2B. Light can be coupled into the fiber 32 from a laser 46 either using a fiber embedded in the PDMS microfluidic system 36 or through an optional external lens 48 which is outside the microfluidic system. The limitation on the latter is that the distance between the edge of the chip and the beginning of the downstream end of the photonic crystal fiber 32 must be less than the depth of focus of the objective lens 48.

The configuration illustrated in FIGS. 2A-2C is particularly useful for concentrating species which are relatively dilute in solution into well defined highly localized and concentrated bands 50. Once collected, these bands 50 can be extracted through any suitable technique, such as downstream microfluidic processing.

Figures 3A, 3B:
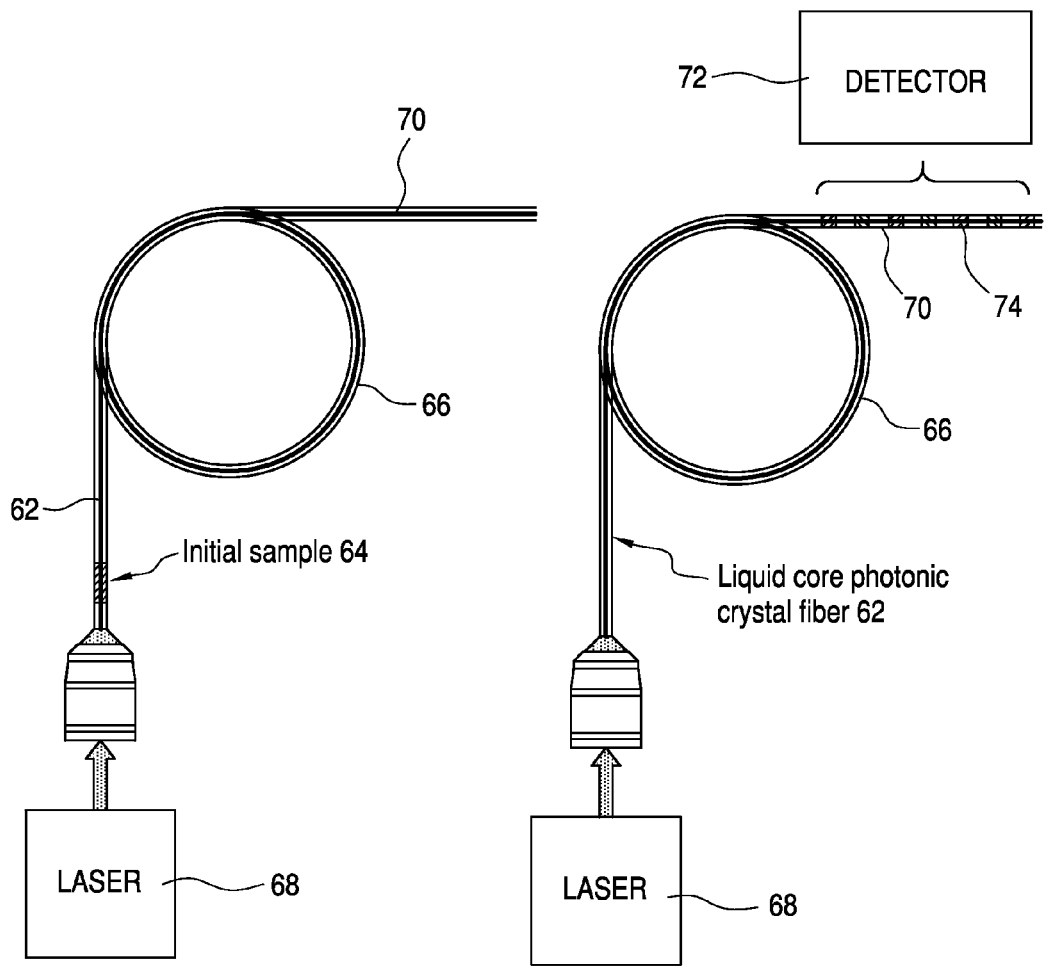
FIGS. 3A and 3B illustrate the operation of a batch implementation of a LCPCF optical chromatography system which is constructed in accordance with a second preferred embodiment of the present invention.

With reference now to FIGS. 3A and 3B, the second preferred embodiment of the present invention comprises an optical chromatography system 60, which is similar to architecture currently used in capillary electrophoresis. In this embodiment, an inlet section of LCPCF 62 feeds a sample plug 64 into a loop of LCPCF 66, which is optically excited as in the previous embodiments by a low power laser 68. The particles in the sample separate after some number of traversals through the LCPCF loop 66 and are then extracted through a LCPCF exit section 70. Particles are introduced into the system identically to how it is done at present in capillary electrophoresis systems. At the end of the fiber 70, any suitable optical or electrical detector 72 detects the separated particles 74 as they pass through the exit section 70. The device level implementation is identical to that shown in FIGS. 1A and 1B, the difference being that in this case the transport would not necessarily be conducted against a gravity or flow field (since the formation of stable, steady state bands is not necessary) and thus a horizontal implementation would likely yield better results. In addition to the fundamental advantages listed above, an additional advantage here would be that the high voltages required for capillary electrophoresis are completely eliminated. These high voltages result in temperature increases along the length of the capillary and ultimately limit the separation efficiency of these systems.

One potential application of the present invention is in the detection of bacteria in waterborne systems. Waterborne bacteria and viral pathogens (such as *Vibrio cholerae, Campylobacter, Salmonella*, and diarrheogenic *Escherichia coli*) from contaminated wells and beaches pose a significant problem in the US and the developing world and, according to the CDC, are responsible for approximately half of the 2 million deaths annually worldwide. There exist three primary difficulties for detecting bacteria in waterborne systems: the lengthy interval required for culturing sufficient bacteria for diagnosis, the low concentration of viable cells typically present (EPA recommends *E. Coli* safety levels in recreational water less than 126 organisms/100 ml) and specific detection from amongst the other organisms present. The current gold standard for detection involves culturing samples and plate counting, both labor intensive and time consuming with an enrichment time of about 24-48 hrs. The optical chromatography system of the present invention would allow concentration and pre-separation of the various competitive organisms on the basis of their significantly different optical and geometric properties (as demonstrated by Hart [18]). Once separated rapid enumeration methods commonly used to detect bacteria in the poultry and beef industries [20] (typically impedance spectroscopy based or optical methods) can be used to determine the composition of each band individually. Such methods typically require on the order of $10^6$-$10^7$ cells/mL which is of the order of the concentration in the bands obtained with during the experiments on the present invention.

Although the invention has been disclosed in terms of a number of preferred embodiments and variations thereon, it will be understood that numerous other variations and modifications could be made thereto without departing from the scope of the invention as defined in the following claims. For example, while the optical chromatography device described herein may most commonly comprise a liquid core waveguiding structure for the separation of particles in a liquid sample, the guiding core of the waveguiding structure can be of any fluid with appropriate properties, including liquids, gases and supercritical fluids. Appropriateness with regards to the fluid's properties is at least in part determined by the fluid's optical properties such as transmissivity and refractive index, and the fluid's physical properties, such as the resistance of the fluid to the movement of particles. Also, note although microfluidic means for inserting the sample into the fluid core of the waveguide is preferable, appropriate non-microfluidic means can also be employed.

REFERENCES

1. Grier D G (2003) A revolution in optical manipulation. Nature 424 (6950): 810-816.
2. Neale S L, Macdonald M P, Dholakia K, and Krauss T F (2005) All-optical control of microfluidic components using form birefringence. Nature Materials 4 (7): 530-533.

3. Chiou P Y, Ohta A T, and Wu M C (2005) Massively parallel manipulation of single cells and microparticles using optical images. Nature 436 (7049): 370-372.
4. Wang M M, Tu E, Raymond D E, Yang J M, Zhang H C, Hagen N, Dees B, Mercer E M, Forster A H, Kariv I, Marchand P J, and Butler W F (2005) Microfluidic sorting of mammalian cells by optical force switching. Nature Biotechnology 23 (1): 83-87.
5. Curtis J E, Koss B A, and Grier D G (2002) Dynamic holographic optical tweezers. Optics Communications 207 (1-6): 169-175.
6. Svoboda K and Block S M (1994) Optical Trapping of Metallic Rayleigh Particles. Optics Letters 19 (13): 930-932.
7. Neuman K C and Block S M (2004) Optical trapping. Review of Scientific Instruments 75 (9): 2787-2809.
8. Ashkin A and Gordon J P (1983) Stability of Radiation-Pressure Particle Traps—an Optical Eamshaw Theorem. Optics Letters 8 (10): 511-513.
9. MacDonald M P, Spalding G C, and Dholakia K (2003) Microfluidic sorting in an optical lattice. Nature 426 (6965): 421-424.
10. Hatano T, Kaneta T, and Imasaka T (1997) Application of optical chromatography to immunoassay. Analytical Chemistry 69 (14): 2711-2715.
11. Imasaka T (1998) Optical chromatography. A new tool for separation of particles. Analusis 26 (5): M53-M55.
12. Makihara J, Kaneta T, and Imasaka T (1999) Optical chromatography: Size determination by eluting particles. Talanta 48 (3): 551-557.
13. Kaneta T, Ishidzu Y, Mishima N, and Imasaka T (1997) Theory of optical chromatography. Analytical Chemistry 69 (14): 2701-2710.
14. Zhao B S, Koo Y M, and Chung D S (2006) Separations based on the mechanical forces of light. Analytica Chimica Acta 556 (1): 97-103.
15. Hart S J and Terray A V (2003) Refractive-index-driven separation of colloidal polymer particles using optical chromatography. Applied Physics Letters 83 (25): 5316-5318.
16. Hart S J, Terray A, Kuhn K L, Arnold J, and Leski T A (2004) Optical chromatography of biological particles. American Laboratory 36 (24): 13-+.
17. Terray A, Arnold J, and Hart S J (2005) Enhanced optical chromatography in a PDMS microfluidic system. Optics Express 13 (25): 10406-10415.
18. Hart S J, Terray A, Leski T A, Arnold J, and Stroud R (2006) Discovery of a significant optical chromatographic difference between spores of *Bacillus anthracis* and its close relative, *Bacillus thuringiensis*. Analytical Chemistry 78 (9): 3221-3225.
19. Mandal S and Erickson D. *Optical Chormatography in Hollow Core Photonic Crystal Fibers*. in *Micro-Total Analysis Systems (uTAS)* 2006. Tokyo.
20. Advances in automated rapid methods for enumerating *E. Coli.*, http://www.foodsafetymagazine.com/issues/0302/colmicro0302.htm

What is claimed is:

1. An optical chromatography device comprising:
a fiber waveguiding structure having a length; a hollow core; and a lattice cladding structure surrounding the hollow core to confine an incident optical beam in the hollow core;
a fluidic module coupled to an inlet terminal of the fiber waveguiding structure to supply a fluid sample containing targets to be separated into the hollow core of said fiber waveguiding structure, wherein the fluid sample has a refractive index greater than an effective refractive index of the lattice cladding structure surrounding the hollow core to confine light within the fluid sample along the hollow core to produce a high optical intensity field inside the fluid sample;
a light source which generates an optical beam;
means for moving said targets in said sample along the length of said core by coupling said optical beam into said core via an inlet terminal of the fiber waveguiding structure and directing said optical beam along the length of said core, thereby applying optical pressure on targets in said fluid sample in a direction along the length of the hollow core which causes said targets to move to different positions along the length of said hollow core to exit the fiber waveguiding structure via an exit terminal of the fiber waveguiding structure based on optical pressure responsive properties of said targets, thereby separating said targets into different target bands at different spatial locations from one target band to another target band along the length of said core; and
a detector located at the exit terminal of the fiber waveguiding structure and operable to detect targets in the different target bands at different spatial locations exiting the exit terminal of the fiber waveguiding structure.

2. The device of claim 1 wherein the fluid in said sample is a liquid.

3. The device of claim 1 wherein the light source is a laser.

4. The device of claim 1 wherein the fiber waveguiding structure is a hollow-core photonic crystal fiber.

5. The device of claim 1, wherein the fiber waveguiding structure is horizontally placed so that the gravity is perpendicular to the length of the hollow core.

6. The device of claim 1, wherein said optical beam is confined in said core by selecting said fiber waveguiding structure to be a photonic crystal fiber having a plurality of air filled capillaries disposed in said lattice cladding structure which make an overall effective index of refraction of said lattice cladding structure to be lower than the index of refraction of said fluid sample, thereby causing total internal reflection of said optical beam in said core.

7. The device of claim 1, wherein the fluidic module includes a reservoir that contains the fluid sample.

8. The device of claim 1, wherein said optical beam is confined in said core by selecting said fiber waveguiding structure to be a photonic crystal fiber having a plurality of air filled capillaries disposed in said lattice cladding structure which form an optical bandgap that confines a band of optical wavelengths in said core and said light source is selected to generate an optical beam having a wavelength in said band of wavelengths.

9. A method for performing optical chromatography comprising the steps of:
using a fiber waveguiding structure having a length of a hollow core; and a lattice cladding structure surrounding said core to receive a fluid sample containing targets to be separated into the hollow core of said fiber waveguiding structure coupling an optical beam into said core to spatially confine and guide light of the optical beam in the fluid sample within the hollow core to produce guided light with a high intensity optical field inside the fluid sample along the length of the hollow core in a way that applies an optical pressure on said targets in said fluid sample along a propagation direction of the guided light along the length of the hollow core that causes said targets to move along said length of said core and to be separated into different target bands at different spatial locations from one target band to another target band from along the length of said core based on optical pressure responsive properties of said targets, without producing a switching on or off an optical force to direct the targets to different directions in the fluid sample; and detecting said targets as they pass through an exit of said fiber waveguiding structure.

10. The method of claim 9, wherein the fluid in said sample is selected to be a liquid.

11. The method of claim 9, wherein the light source is selected to be a laser.

12. The method of claim 9, wherein the fiber waveguiding structure is selected to be a hollow-core photonic crystal fiber.

13. The method of claim 12, wherein the sample fluid is selected to be a liquid and the light source is selected to be a laser.

14. The method of claim 9, wherein said optical beam is confined in said core by selecting said waveguide to be a photonic crystal fiber having a plurality of air filled capillaries disposed in said lattice cladding structure and selecting said fluid in said sample to have an index of refraction that is greater than an overall effective index of refraction of said lattice cladding structure, thereby causing total internal reflection of said optical beam in said core.

15. The method of claim 14, wherein said fluid in said sample is selected to be a liquid.

16. The method of claim 9, wherein said optical beam is confined in said core by selecting said waveguide to be a photonic crystal fiber having a plurality of air filled capillaries disposed in said lattice cladding structure which form an optical bandgap that confines a band of optical wavelengths in said core and said light source is selected to generate an optical beam having a wavelength in said band of wavelengths.

17. The method of claim 9, wherein the step of inserting a fluid sample containing targets to be separated into the hollow core of said waveguiding structure further comprises applying a flow pressure to said fluid sample which is counter to the optical pressure imparted by said optical beam, whereby said flow pressure and said optical pressure thereby cause said targets to be separated into a plurality of bands along the length of said core based on the optical pressure responsive properties of said targets.

18. The method of claim 17, wherein the electro osmotic flow pressure is employed to introduce said sample into said core and to counter said optical pressure.

19. The method of claim 9, in which said targets are separated from one another based on their size relative to one another.

20. The device of claim 1, wherein said means for inserting a fluid sample containing targets to be separated into the hollow core of said waveguiding structure is configured to apply a flow pressure on said targets which counters the optical pressure, whereby said flow pressure and said optical pressure thereby cause said targets to be separated into a plurality of bands along the length of said core based on the optical pressure responsive properties of said targets.

21. The device of claim 20, wherein the electro osmotic flow pressure is employed to introduce said sample into said core and counter said optical pressure.

22. The device of claim 1, in which said targets are separated based on their size relative to one another.

23. The device of claim 1, in which said fiber waveguiding structure is in the form of a loop having an inlet for receiving targets to be separated and an exit for removing from said loop targets that have been separated, said loop being configured to allow targets to traverse said loop more than once prior to being removed from said loop through said exit.

24. The device of claim 23, wherein the length said fiber waveguiding structure is at least one meter.

25. The device of claim 1, wherein the length said fiber waveguiding structure is at least one meter.

26. The method of claim 9, wherein said fiber waveguiding structure includes a loop having an inlet for receiving targets to be separated and an exit for removing from said loop targets that have been separated; and said step of moving said targets along the length of said core comprises moving said targets through said loop more than once; and then removing said targets from said loop through said exit.

27. The method of claim 26, wherein the length of said loop is at least one meter.

28. The method of claim 9, wherein the length said fiber waveguiding structure is at least one meter.

29. The device as in claim 1, comprising:
a DC circuit electrically coupled to the inlet and exit terminals of the fiber waveguiding structure to apply a DC voltage to the fluid sample to cause an electrokinetic transport flow in a direction from the exit terminal to the inlet terminal that is opposite to the propagation direction of the guided light in the hollow core to counter the optical pressure exerted on the targets in the fluid sample caused by the guided light to form the target bands at the different locations.

30. A method for performing optical chromatography on particles of different sizes suspended in a fluid, comprising: using a fiber waveguiding structure having a length of a hollow core; and a lattice cladding structure surrounding said core to receive fluid particles of different sizes to be separated; applying a DC voltage to the fluid to cause an electrokinetic transport flow in a first direction in the hollow core of the fiber waveguiding structure; coupling an optical beam into the hollow core along a second direction opposite to the first direction to produce optical pressure on the particles in the fluid to cause the particles in the fluid to move along the second direction to counter the electrokinetic transport flow in the first direction in the hollow core so that the particles in the fluid are separated in different particle bands at different spatial locations from one particle band to another; and detecting particles in the different particle bands to obtain properties of the different particle bands.

31. The method as in claim 30, comprising:
using a photonic crystal fiber with a hollow center as the fiber waveguiding structure.

32. The method as in claim 30, wherein the fluid is a gas.

33. The method as in claim 30, wherein the fluid is a liquid.

34. The method as in claim 33, wherein the particles are biological particles.

35. The method as in claim 34, wherein the particles include bacteria.

36. The method as in claim 34, wherein the particles include cells.

* * * * *